United States Patent
Clarke et al.

(10) Patent No.: US 9,964,546 B1
(45) Date of Patent: May 8, 2018

(54) C PEPTIDE DETECTION BY MASS SPECTROMETRY

(71) Applicant: Quest Diagnostics Investments Incorporated, Wilmington, DE (US)

(72) Inventors: Nigel Clarke, Vista, CA (US); Zhaohui Chen, Las Flores, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days. days.

(21) Appl. No.: 15/888,681

(22) Filed: Feb. 5, 2018

Related U.S. Application Data

(63) Continuation of application No. 15/457,683, filed on Mar. 13, 2017, now Pat. No. 9,885,724, which is a continuation of application No. 14/654,964, filed as application No. PCT/US2013/077575 on Dec. 23, 2013, now Pat. No. 9,594,074.

(60) Provisional application No. 61/745,976, filed on Dec. 26, 2012.

(51) Int. Cl.
*G01N 33/68* (2006.01)
*G01N 30/72* (2006.01)
*H01J 49/16* (2006.01)
*H01J 49/40* (2006.01)
*H01J 49/00* (2006.01)

(52) U.S. Cl.
CPC ..... *G01N 33/6848* (2013.01); *G01N 30/7266* (2013.01); *G01N 2560/00* (2013.01); *H01J 49/005* (2013.01); *H01J 49/165* (2013.01); *H01J 49/40* (2013.01)

(58) Field of Classification Search
USPC .................. 250/282, 281; 436/86; 435/4, 23
See application file for complete search history.

(56) References Cited

U.S. PATENT DOCUMENTS

| | | | |
|---|---|---|---|
| 2009/0148951 A1* | 6/2009 | Zhang ................ | G01N 33/6848 436/86 |
| 2012/0164741 A1* | 6/2012 | Chen ...................... | G01N 33/74 436/86 |
| 2016/0282328 A1* | 9/2016 | Taylor .................... | G01N 33/49 |

* cited by examiner

*Primary Examiner* — Kiet T Nguyen
(74) *Attorney, Agent, or Firm* — Quest Diagnostics, Inc.

(57) ABSTRACT

Methods are described for measuring the amount of C peptide in a sample. More specifically, mass spectrometric methods are described for detecting and quantifying C peptide in a sample utilizing on-line extraction methods coupled with tandem mass spectrometric or high resolution/high accuracy mass spectrometric techniques.

11 Claims, 10 Drawing Sheets

Full MS scan spectrum showing possible C peptide precursor ions

C PEPTIDE DETECTION BY MASS SPECTROMETRY

CROSS-REFERENCE TO RELATED APPLICATIONS

This application is a continuation of U.S. application Ser. No. 15/457,683, filed Mar. 13, 2017, which is a continuation of U.S. application Ser. No. 14/654,964, filed Jun. 23, 2015, now U.S. Pat. No. 9,594,074, which is a national stage application of International Application No. PCT/US2013/077575, filed Dec. 23, 2013, which claims the benefit under 35 U.S.C. § 119(e) to U.S. Provisional Application Ser. No. 61/745,976, filed Dec. 26, 2012, the contents of which are incorporated by reference in their entirety into the present disclosure.

FIELD OF THE INVENTION

The invention relates to the quantitative measurement of C peptide. In a particular aspect, the invention relates to methods for quantitative measurement of C peptide by mass spectrometry.

BACKGROUND OF THE INVENTION

The following description of the background of the invention is provided simply as an aid in understanding the invention and is not admitted to describe or constitute prior art to the invention.

C peptide is a peptide that is formed as part of the process of proinsulin conversion (via cleavage) to insulin before release from endocytic vesicles within the pancreas. Human C peptide has a molar mass of about 3020.3 amu.

C peptide binds to receptors at the cell surface and activates signal transduction pathways that result in stimulation of Na+, K+ ATPase and endothelial nitric oxide synthase (eNOS). Both of these enzymes have reduced activities in type 2 diabetes. C peptide also functions in repair of the muscular layer of the arteries.

C peptide levels instead of insulin are often measured in newly diagnosed diabetes patients because insulin concentration in the portal vein can range from two to ten times higher than in the peripheral circulation. The liver extracts about half of the insulin from plasma, but this varies with the nutritional state of the subject. Thus, C peptide may be a more comprehensive indicator of insulin status than direct insulin measurement. Patients with type 1 diabetes are unable to produce insulin efficiently and therefore will have a decreased level of C peptide, while C peptide levels in patients with type 2 diabetes are typically normal or even elevated. Thus, C peptide measurement is used to distinguish type 1 diabetes from type 2 diabetes. Additionally, as C peptide is formed during natural insulin production, measuring C peptide in patients undergoing insulin therapy may help determine how much natural insulin the patient is producing.

C peptide measurement can also be used to determine if a patient may have a gastrinoma associated with Multiple Endocrine Neoplasm syndrome. A significant number of Multiple Endocrine Neoplasm syndromes presenting with gastrinoma also include pancreatic, parathyroid, and pituitary adenomas. Higher levels of C peptide together with the presence of a gastrinoma suggests that organs other than the stomach may harbor a neoplasm. C peptide may also be assessed in patients suspected of insulin abuse, and in women with Polycystic Ovary Syndrome to assess degree of insulin resistance.

SUMMARY OF THE INVENTION

The present invention provides methods for detecting the presence or amount of C peptide in a sample by mass spectrometry.

Some embodiments presented herein utilize tandem mass spectrometry. In some of these embodiments, the methods include: (a) subjecting a sample suspected of containing C peptide to high performance liquid chromatography (HPLC) to obtain a fraction enriched in C peptide; (b) subjecting the enriched C peptide to an ionization source under conditions suitable to generate one or more C peptide ions detectable by mass spectrometry; (c) determining the amount of one or more C peptide ions by tandem mass spectrometry, wherein the determined ions comprise a precursor ion with a mass to charge ratio of 1007.5±0.5 and one or more fragment ions selected from the group of ions with mass to charge ratios consisting of 927.6±0.5, 785.4±0.5, and 646.1±0.5. In these embodiments, the amount of the one or more ions determined in step (c) is related to the amount of C peptide in the sample, e.g., used to determine the amount of C peptide in the sample. In some embodiments, the HPLC is 1-D HPLC. In some embodiments, the amounts of two or more fragment ions selected from the group consisting of 927.6±0.5, 785.4±0.5, and 646.1±0.5 are determined in step (c).

In other embodiments utilizing tandem mass spectrometry, the methods include: (a) subjecting the sample to 1-D high performance liquid chromatography (1-D HPLC) to obtain a fraction enriched in C peptide; (b) subjecting the fraction enriched in C peptide to an ionization source under conditions suitable to generate one or more C peptide ions detectable by mass spectrometry; and (c) determining the amount of one or more C peptide ions by tandem mass spectrometry. In these embodiments, the amount of ions determined in step (c) is related to the amount of a C peptide in the sample. In some embodiments, the one or more ions detected in step (c) comprise a precursor ion with a mass to charge ratio (m/z) of about 1007.5±0.5. In some related embodiments, the one or more ions detected in step (c) further comprise one or more fragment ions selected from the group of ions with mass to charge ratios (m/z) of about 927.6±0.5, 785.4±0.5, and 646.1±0.5. In some related embodiments, the one or more ions detected in step (c) comprise two or more fragment ions selected from the group of ions with mass to charge ratios (m/z) of about 927.6±0.5, 785.4±0.5, and 646.1±0.5.

In embodiments utilizing tandem mass spectrometry, tandem mass spectrometry may be conducted by any method known in the art, including for example, multiple reaction monitoring, precursor ion scanning, or product ion scanning.

In some embodiments, tandem mass spectrometry comprises fragmenting a precursor ion with a mass to charge ratio of 1007.5±0.50 into one or more fragment ions. In certain related embodiments, the one or more fragment ions comprise one or more ions selected from the group consisting of ions with mass to charge ratios of 927.6±0.5, 785.4±0.5, 646.1±0.5, 147.0±0.5, and 260.3±0.5. In other related embodiments, the one or more fragment ions comprise one or more ions selected from the group consisting of ions with mass to charge ratios of 927.6±0.5, 785.4±0.5, 646.1±0.5. In embodiments where the amounts of two or more fragment ions are determined, the amounts may be subject to any mathematical manipulation known in the art in order to relate the measured ion amounts to the amount of C peptide in the sample. For example, the amounts of two or more fragment ions may be summed as part of determining the amount of C peptide in the sample.

Some embodiments presented herein utilizing high resolution/high accuracy mass spectrometry. In some of these embodiments, the methods include: (a) subjecting a sample suspected of containing C peptide to high performance liquid chromatography (HPLC) to obtain a fraction enriched in C peptide; (b) subjecting the fraction enriched in C peptide to an ionization source under conditions suitable to generate one or more C peptide ions detectable by mass spectrometry; and (c) determining the amount of one or more C peptide ions by high resolution/high accuracy mass spectrometry. In these embodiments, the amount of ions determined in step (c) is related to the amount of C peptide in the sample.

In some embodiments, high resolution/high accuracy spectrometry is conducted at a resolving power or FWHM (Full Width at Half Maximum) of 10,000 and a mass accuracy of 50 ppm. In some embodiments, the high resolution/high accuracy mass spectrometer is a high resolution/high accuracy time-of-flight (TOF) mass spectrometer. In some embodiments, HPLC is 1-D HPLC. In some embodiments, the one or more ions determined in step (c) comprise an ion with a charge of 2+ or 3+. In some embodiments, the one or more ions determined in step (c) comprise an ion selected from the group of ions with a mass to charge ratio (m/z) within the ranges of about $1007.5\pm1$ and $1510.3\pm1$.

In some embodiments, the high resolution/high accuracy mass spectrometry is conducted at a resolving power (FWHM) of greater than or equal to about 10,000, such as greater than or equal to about 15,000, such as greater than or equal to about 20,000, such as greater than or equal to about 25,000. In some embodiments, the high resolution/high accuracy mass spectrometry is conducted at an accuracy of less than or equal to about 50 ppm, such as less than or equal to about 20 ppm, such as less than or equal to about 10 ppm, such as less than or equal to about 5 ppm; such as less than or equal to about 3 ppm. In some embodiments, high resolution/high accuracy mass spectrometry is conducted at a resolving power (FWHM) of greater than or equal to about 10,000 and an accuracy of less than or equal to about 50 ppm. In some embodiments, the resolving power is greater than about 15,000 and the accuracy is less than or equal to about 20 ppm. In some embodiments, the resolving power is greater than or equal to about 20,000 and the accuracy is less than or equal to about 10 ppm; preferably resolving power is greater than or equal to about 20,000 and accuracy is less than or equal to about 5 ppm, such as less than or equal to about 3 ppm.

In some embodiments, the high resolution/high accuracy mass spectrometry may be conducted with an orbitrap mass spectrometer, a time of flight (TOF) mass spectrometer, or a Fourier transform ion cyclotron resonance mass spectrometer (sometimes known as a Fourier transform mass spectrometer).

In any of the methods described herein, the sample may comprise a biological sample. In some embodiments, the biological sample may comprise a body fluid such as urine, plasma, or serum. In some embodiments, the biological sample may comprise a sample from a human; such as from an adult male or female, or juvenile male or female, wherein the juvenile is under age 18, under age 15, under age 12, or under age 10. The human sample may be analyzed to diagnose or monitor a disease state or condition, or to monitor therapeutic efficacy of treatment of a disease state or condition. In some related embodiments, the methods described herein may be used to determine the amount of C peptide in a biological sample when taken from a human.

In embodiments utilizing either tandem mass spectrometry or high resolution/high accuracy mass spectrometry, the sample may be subjected to high performance liquid chromatography (HPLC) prior to ionization.

In embodiments utilizing either tandem mass spectrometry or high resolution/high accuracy mass spectrometry, the sample may be subjected to an extraction column, such as a solid phase extraction (SPE) column, prior to being subjected to an analytical column, such as a high performance liquid chromatography (HPLC) column. In some related embodiments, the extraction column is not an immunopurification column (i e, an immunoaffinity column). In some embodiments, immunopurification is not used at any point in the method. In alternate embodiments, C peptide is extracted from the sample with an immunopurification technique; such as with an immunoaffinity extraction column.

In embodiments which utilize two or more of an extraction column such as a solid phase extraction column (SPE), an analytical column such as a high performance liquid chromatography (HPLC) column, and an ionization source, two or more of these components may be connected in an on-line fashion to allow for automated sample processing and analysis.

In any of the methods presented herein, the sample may comprise a biological sample; such as a body fluid sample, including, for example, plasma or serum.

Mass spectrometry (either tandem or high resolution/high accuracy) may be performed in positive ion mode. Alternatively, mass spectrometry may be performed in negative ion mode. Various ionization sources, including for example atmospheric pressure chemical ionization (APCI) or electrospray ionization (ESI), may be used to ionize C peptide. In some embodiments, C peptide is ionized by ESI in positive ion mode.

In any method presented herein, a separately detectable internal standard may be provided in the sample, the amount of which is also determined in the sample. In embodiments utilizing a separately detectable internal standard, all or a portion of both the analyte of interest and the internal standard present in the sample is ionized to produce a plurality of ions detectable in a mass spectrometer, and one or more ions produced from each are detected by mass spectrometry. In these embodiments, the presence or amount of ions generated from the analyte of interest may be related to the presence of amount of analyte of interest in the sample by comparison to the amount of internal standard ions detected.

Alternatively, the amount of the C peptide in a sample may be determined by comparison to one or more external reference standards. Exemplary external reference standards include blank plasma or serum spiked with C peptide or an isotopically labeled variant thereof.

In some embodiments, the methods demonstrate a linear range for detection of C peptide at levels at least within the range of about 0.049 ng/50 μL to 25 ng/50 μL.

As used herein, unless otherwise stated, the singular forms "a," "an," and "the" include plural reference. Thus, for example, a reference to "a protein" includes a plurality of protein molecules.

As used herein, the terms "purification", "purifying", and "enriching" do not refer to removing all materials from the sample other than the analyte(s) of interest. Instead, these terms refer to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "immunopurification" or "immunopurify" refers to a purification procedure that utilizes antibodies, including polyclonal or monoclonal antibodies, to enrich the one or more analytes of interest. Immunopurification can be performed using any of the immunopurification methods well known in the art. Often the immunopurification procedure utilizes antibodies bound, conjugated or otherwise attached to a solid support, for example a column, well, tube, gel, capsule, particle or the like. Immunopurification as used herein includes without limitation procedures often referred to in the art as immunoprecipitation, as well as procedures often referred to in the art as affinity chromatography or immunoaffinity chromatography.

As used herein, the term "immunoparticle" refers to a capsule, bead, gel particle or the like that has antibodies bound, conjugated or otherwise attached to its surface (either on and/or in the particle). In certain preferred embodiments, immunoparticles are sepharose or agarose beads. In alternative preferred embodiments, immunoparticles comprise glass, plastic or silica beads, or silica gel.

As used herein, the term "anti-C peptide antibody" refers to any polyclonal or monoclonal antibody that has an affinity for C peptide. In various embodiments the specificity of C peptide antibodies to chemical species other than C peptide may vary; for example in certain preferred embodiments the anti-C peptide antibodies are specific for C peptide and thus have little or no affinity for chemical species other than C peptide, whereas in other preferred embodiments the anti-C peptide antibodies are non-specific and thus bind certain chemical species other than C peptide.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In certain embodiments, the sample comprises a body fluid sample from a human; such as plasma or serum.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

Generally, the affinity of a SPE column packing material for an analyte may be due to any of a variety of mechanisms, such as one or more chemical interactions or an immunoaffinity interaction. In some embodiments, SPE of C peptide is conducted without the use of an immunoaffinity column packing material. That is, in some embodiments, insulin is purified from a sample by a SPE column that is not an immunoaffinity column.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column. The term "1-D high performance liquid chromatography" or "1-D HPLC" refers to traditional, single column HPLC. The term "2-D high performance liquid chromatography" refers to a high performance liquid chromatography technique where two HPLC columns are used in such a way that the analyte and any additional species that co-elute at the same time as the analyte are directed from a first HPLC column onto a second HPLC column with a different stationary phase. The stationary phase of the second HPLC column is selected such that the analyte and co-eluting species are separated before introduction of the analyte to a mass spectrometric instrument. 2-D HPLC typically is more costly in terms of run time and requires additional complexity of set-up relative to 1-D HPLC; however, in particularly complex samples, greater analyte purity may be achieved with 2-D HPLC compared to 1-D HPLC.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in substantially straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., "Turbulent Flow Analysis: Measurement and Prediction," P. S. Bernard & J. M. Wallace, John Wiley & Sons, Inc., (2000); "An Introduction to Turbulent Flow," Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 µm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 5 µm in diameter.

As used herein, the terms "on-line" and "inline", for example as used in "on-line automated fashion" or "on-line extraction", refers to a procedure performed without the need for operator intervention. In contrast, the term "off-line" as used herein refers to a procedure requiring manual intervention of an operator. Thus, if samples are subjected to precipitation and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer, a mass analyzer, and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, "high resolution/high accuracy mass spectrometry" refers to mass spectrometry conducted with a mass analyzer capable of measuring the mass to charge ratio of a charged species with sufficient precision and accuracy to confirm a unique chemical ion. Confirmation of a unique chemical ion is possible for an ion when individual isotopic peaks from that ion are readily discernable. The particular resolving power and mass accuracy necessary to confirm a unique chemical ion varies with the mass and charge state of the ion.

As used herein, the term "resolving power" or "resolving power (FWHM)" (also known in the art as "$m/\Delta m_{50\%}$") refers to an observed mass to charge ratio divided by the width of the mass peak at 50% maximum height (Full Width Half Maximum, "FWHM"). The effect of differences in resolving power is illustrated, for example, in FIGS. 1A-C of co-pending U.S. Patent Publication No. 2011/0111512, which is incorporated by reference herein.

As used herein a "unique chemical ion" with respect to mass spectrometry refers a single ion with a single atomic makeup. The single ion may be singly or multiply charged.

As used herein, the term "accuracy" (or "mass accuracy") with respect to mass spectrometry refers to potential deviation of the instrument response from the true m/z of the ion investigated. Accuracy is typically expressed in parts per million (ppm). The effect of differences in mass accuracy is illustrated, for example, in FIGS. 2A-D of co-pending U.S. Patent Publication No. 2011/0111512, which is incorporated by reference herein.

High resolution/high accuracy mass spectrometry methods of the present invention may be conducted on instruments capable of performing mass analysis with FWHM of greater than 10,000, 15,000, 20,000, 25,000, 50,000, 100,000, or even more. Likewise, methods of the present invention may be conducted on instruments capable of performing mass analysis with accuracy of less than 50 ppm, 20 ppm, 15 ppm, 10 ppm, 5 ppm, 3 ppm, or even less. Instruments capable of these performance characteristics may incorporate certain orbitrap mass analyzers, time-of-flight ("TOF") mass analyzers, or Fourier-transform ion cyclotron resonance mass analyzers. In preferred embodiments, the methods are carried out with an instrument which includes an orbitrap mass analyzer or a TOF mass analyzer.

The term "orbitrap" describes an ion trap consisting of an outer barrel-like electrode and a coaxial inner electrode. Ions are injected tangentially into the electric field between the electrodes and trapped because electrostatic interactions between the ions and electrodes are balanced by centrifugal forces as the ions orbit the coaxial inner electrode. As an ion orbits the coaxial inner electrode, the orbital path of a trapped ion oscillates along the axis of the central electrode at a harmonic frequency relative to the mass to charge ratio of the ion. Detection of the orbital oscillation frequency allows the orbitrap to be used as a mass analyzer with high accuracy (as low as 1-2 ppm) and high resolving power (FWHM) (up to about 200,000). A mass analyzer based on an orbitrap is described in detail in U.S. Pat. No. 6,995,364, incorporated by reference herein in its entirety. Use of orbitrap analyzers has been reported for qualitative and quantitative analyses of various analytes. See, e.g., U.S. Patent Application Pub. No. 2008/0118932 (filed Nov. 9, 2007); Bredehöft, et al., Rapid Commun. Mass Spectrom., 2008, 22:477-485; Le Breton, et al., Rapid Commun. Mass Spectrom., 2008, 22:3130-36; Thevis, et al., Mass Spectrom. Reviews, 2008, 27:35-50; Thomas, et al., J. Mass Spectrom., 2008, 43:908-15; Schenk, et al., BMC Medical Genomics, 2008, 1:41; and Olsen, et al., Nature Methods, 2007, 4:709-12.

As used herein, the term "operating in negative ion mode" refers to those mass spectrometry methods where negative ions are generated and detected. The term "operating in positive ion mode" as used herein, refers to those mass spectrometry methods where positive ions are generated and detected. In preferred embodiments, mass spectrometry is conducted in positive ion mode.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e g ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photoionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the ionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 85% to 115%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

DETAILED DESCRIPTION OF THE INVENTION

Figure 1:
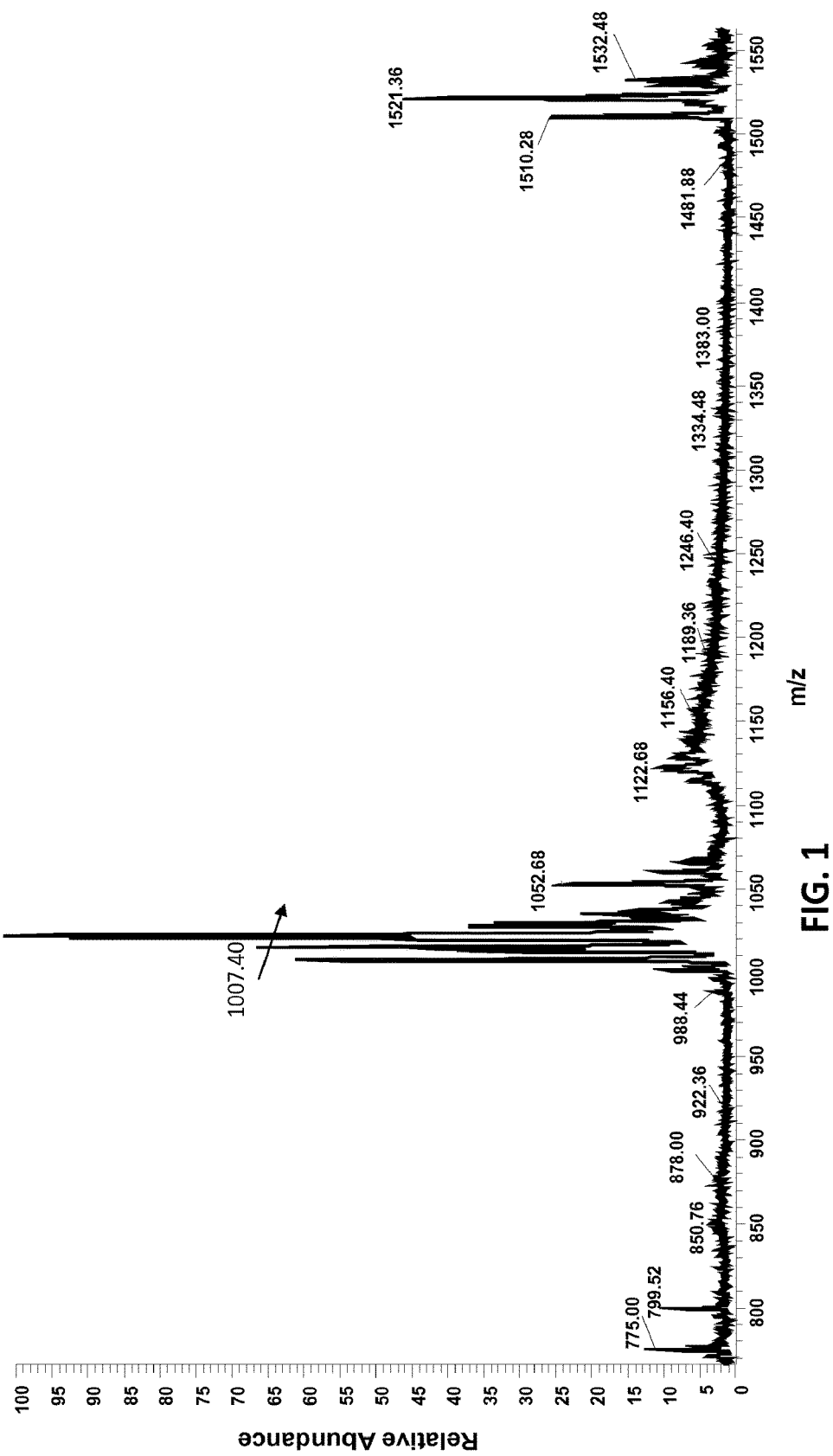
FIG. 1 shows a full scan mass spectrum showing possible C peptide precursor ions. Details are discussed in Example 3.

Methods are described for measuring the amount of C peptide in a sample. More specifically, mass spectrometric methods are described for detecting and quantifying C peptide in a sample. The methods may utilize solid phase extraction (SPE) and/or liquid chromatography (LC), to perform a purification of selected analytes, combined with methods of mass spectrometry (MS), thereby providing an assay system for detecting and quantifying C peptide in a sample. The preferred embodiments are particularly well suited for application in large clinical laboratories for automated C peptide quantification assay.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma and serum. Such samples may be obtained, for example, from a patient; that is, a living person, male or female, presenting oneself in a clinical setting for diagnosis, prognosis, or treatment of a disease or condition. In embodiments where the sample comprises a biological sample, the methods may be used to determine the amount of C peptide in the sample when the sample was obtained from the biological source (i.e., the amount of endogenous C peptide in the sample).

The present invention also contemplates kits for a C peptide quantitation assay. A kit for a C peptide quantitation assay may include a kit comprising the compositions provided herein, such as an external reference standard. The external reference standard, in some aspects, includes blank plasma or serum spiked with C peptide or an isotopically labeled variant thereof. For example, a kit may include packaging material and measured amounts of an isotopically labeled internal standard, in amounts sufficient for at least one assay. Typically, the kits will also include instructions recorded in a tangible form (e.g., contained on paper or an electronic medium) for using the packaged reagents for use in a C peptide quantitation assay.

Calibration and QC pools for use in embodiments of the present invention are preferably prepared using a matrix similar to the intended sample matrix, provided that C peptide is essentially absent.

Sample Preparation for Mass Spectrometric Analysis

In preparation for mass spectrometric analysis, C peptide may be enriched relative to one or more other components in the sample by various methods known in the art, including for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

One method of sample purification that may be used prior to mass spectrometry is applying a sample to a solid-phase extraction (SPE) column under conditions where the analyte of interest is reversibly retained by the column packing material, while one or more other materials are not retained. In this technique, a first mobile phase condition can be employed where the analyte of interest is retained by the column, and a second mobile phase condition can subsequently be employed to remove retained material from the column, once the non-retained materials are washed through.

In some embodiments, C peptide in a sample may be reversibly retained on a SPE column with a packing material comprising an alkyl bonded surface. For example, in some embodiments, a C-8 on-line SPE column (such as a Strata C-8 on-line SPE column (20 mm×2.0 mm) from Phenomenex, Inc. or equivalent) may be used to enrich C peptide prior to mass spectrometric analysis. In some embodiments, use of an SPE column is conducted with HPLC Grade 0.1% aqueous formic acid as a wash solution, and use of 0.1% formic acid in acetonitrile as an elution solution.

In some embodiments, C peptide is not purified by any immunoaffinity technique. Some of these embodiments utilize a SPE column. In these embodiments, the SPE column is not an immunoaffinity column.

In other embodiments, the methods include immunopurifying C peptide prior to mass spectrometry analysis. The immunopurification step may be performed using any of the immunopurification methods well known in the art. Often the immunopurification procedure utilizes antibodies bound, conjugated, immobilized or otherwise attached to a solid support, for example a column, well, tube, capsule, particle or the like. Generally, immunopurification methods involve (1) incubating a sample containing the analyte of interest with antibodies such that the analyte binds to the antibodies, (2) performing one or more washing steps, and (3) eluting the analyte from the antibodies.

In certain embodiments the incubation step of the immunopurification is performed with the antibodies free in solution and the antibodies are subsequently bound or attached to a solid surface prior to the washing steps. In certain embodiments this can be achieved using a primary antibody that is an anti-C peptide antibody and a secondary antibody attached to a solid surface that has an affinity to the primary anti-C peptide antibody. In alternative embodiments, the primary antibody is bound to the solid surface prior to the incubation step.

Appropriate solid supports include without limitation tubes, slides, columns, beads, capsules, particles, gels, and the like. In some preferred embodiments, the solid support is a multi-well plate, such as, for example, a 96 well plate, a 384-well plate or the like. In some embodiments the solid support are sepharose or agarose beads or gels. There are numerous methods well known in the art by which antibodies (for example, an anti-C peptide antibody or a secondary antibody) may be bound, attached, immobilized or coupled to a solid support, e.g., covalent or non-covalent linkages adsorption, affinity binding, ionic linkages and the like. In some embodiments antibodies are coupled using CNBr, for example the antibodies may be coupled to CNBr activated sepharose. In other embodiments, the antibody is attached to the solid support through an antibody binding protein such as protein A, protein G, protein A/G, or protein L.

The washing step of the immunopurification methods generally involve washing the solid support such that the C peptide remain bound to the anti-C peptide antibodies on the solid support. The elution step of the immunopurification generally involves the addition of a solution that disrupts the binding of C peptide to the anti-C peptide antibodies. Exemplary elution solutions include organic solutions, salt solutions, and high or low pH solutions.

Another method of sample purification that may be used prior to mass spectrometry is liquid chromatography (LC). In liquid chromatography techniques, an analyte may be purified by applying a sample to a chromatographic analytical column under mobile phase conditions where the analyte of interest elutes at a differential rate in comparison to one or more other materials. Such procedures may enrich the amount of one or more analytes of interest relative to one or more other components of the sample.

Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a partition process and may select LC, including HPLC, instruments and columns that are suitable for use with C peptide. The chromatographic analytical column typically includes a medium (i.e., a packing material) to facilitate separation of chemical moieties (i.e., fractionation). The medium may include minute particles. The particles typically include a bonded surface that interacts with the various chemical moieties to facilitate separation of the chemical moieties. One suitable bonded surface is a hydrophobic bonded surface such as an alkyl bonded or a cyano bonded surface. Alkyl bonded surfaces may include C-4, C-8, C-12, or C-18 bonded alkyl groups. In some embodiments, the chromatographic analytical column is a monolithic C-18 column. The chromatographic analytical column includes an inlet port for receiving a sample and an outlet port for discharging an effluent that includes the fractionated sample. The sample may be supplied to the inlet port directly, or from a SPE column, such as an on-line SPE column or a TFLC column. In some embodiments, an on-line filter may be used ahead of the SPE column and or HPLC column to remove particulates and phospholipids in the samples prior to the samples reaching the SPE and/or TFLC and/or HPLC columns.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In some embodiments, C peptide in a sample is enriched with HPLC. This HPLC may be 1-D HPLC conducted with a monolithic C-18 column chromatographic system, for example, an Onyx Monolithic C-18 column from Phenomenex Inc. (50×2.0 mm), or equivalent. In certain embodiments, HPLC is performed using HPLC Grade 0.1% aqueous formic acid as a wash solution, and, and 0.1% formic acid in acetonitrile as an elution solution.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, one or more of the above purification techniques may be used in parallel for purification of C peptide to allow for simultaneous processing of multiple samples. In some embodiments, the purification techniques employed exclude immunopurification techniques, such as immunoaffinity chromatography.

In some embodiments, TFLC may be used for purification of C peptide prior to mass spectrometry. In such embodiments, samples may be extracted using a TFLC column which captures the analyte. The analyte is then eluted and transferred on-line to an analytical HPLC column. For example, sample extraction may be accomplished with a TFLC extraction cartridge with a large particle size (50 μm) packing. Sample eluted off of this column may then be transferred on-line to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

Detection and Quantitation of C Peptide by Mass Spectrometry

Mass spectrometry is performed using a mass spectrometer, which includes an ion source for ionizing the fractionated sample and creating charged molecules for further analysis. In various embodiments, C peptide may be ionized by any method known to the skilled artisan. For example ionization of C peptide may be performed by electron ionization, chemical ionization, electrospray ionization (ESI), photon ionization, atmospheric pressure chemical ionization (APCI), photoionization, atmospheric pressure photoionization (APPI), Laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc. C peptide may be ionized in positive or negative mode. In preferred embodiments, C peptide is ionized by ESI in positive ion mode.

In mass spectrometry techniques generally, after the sample has been ionized, the positively or negatively charged ions thereby created may be analyzed to determine a mass-to-charge ratio (m/z). Various analyzers for determining m/z include quadrupole analyzers, ion traps analyzers, time-of-flight analyzers, Fourier transform ion cyclotron resonance mass analyzers, and orbitrap analyzers. Some exemplary ion trap methods are described in Bartolucci, et al., *Rapid Commun. Mass Spectrom.* 2000, 14:967-73.

The ions may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM). In some embodiments, the mass-to-charge ratio is determined using a quadrupole analyzer. In a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of C peptide. The relative abundance of a given ion may be converted into an absolute amount of the original analyte using calibration standard curves based on peaks of one or more ions of an internal or external molecular standard.

One may enhance the resolution of MS techniques employing certain mass spectrometric analyzers through "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples. In certain embodiments, a mass spectrometric instrument with multiple quadrupole analyzers (such as a triple quadrupole instrument) is employed to conduct tandem mass spectrometric analysis.

In certain embodiments using a MS/MS technique, precursor ions are isolated for further fragmentation and collision activated dissociation (CAD) is used to generate fragment ions from the precursor ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some embodiments, C peptide in a sample is detected and/or quantified using MS/MS as follows. C peptide is enriched in a sample by first subjecting the sample to SPE, then to liquid chromatography, preferably HPLC, such as 1-D HPLC; the flow of liquid solvent from a chromatographic analytical column enters the heated nebulizer interface of an MS/MS analyzer; and the solvent/analyte mixture is converted to vapor in the heated charged tubing of the interface. During these processes, the analyte (i.e., C peptide) is ionized. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the m/z of a C peptide precursor ion. Precursor ions with the correct m/z are allowed to pass into the collision chamber (Q2), while unwanted ions with any other m/z collide with the sides of the quadrupole and are eliminated. Precursor ions entering Q2 collide with neutral gas molecules (such as Argon molecules) and fragment. The fragment ions generated are passed into quadrupole 3 (Q3), where the C peptide fragment ions are selected while other ions are eliminated.

The methods may involve MS/MS performed in either positive or negative ion mode; in some embodiments the MS/MS is performed in positive ion mode. In certain embodiments, Q1 selects for precursor ions with an m/z of about 1007.5±0.5. In related embodiments, Q3 may select fragment ions with m/z of about 927.6±0.5, and/or 785.4±0.5, and/or 646.1±0.5. In certain embodiments, the relative abundance of a single fragment ion may be measured. Alternatively, the relative abundances of two or more fragment ions may be measured. In these embodiments, the relative abundances of each fragment ion may be summed to quantitatively assess C peptide originally in the sample.

Alternate modes of operating a tandem mass spectrometric instrument that may be used in certain embodiments include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

In other embodiments, a high resolution/high accuracy mass analyzer may be used for quantitative analysis of C peptide according to methods of the present invention. To obtain acceptable level of quantitative results, the mass spectrometer must be capable of exhibiting a resolving power (FWHM) of 10,000 or higher, with accuracy of about 50 ppm or less for the ions of interest; preferably the mass spectrometer exhibits a resolving power (FWHM) of 18,000 or higher and accuracy of about 5 ppm or less; such as a resolving power (FWHM) of 20,000 or higher and accuracy of about 3 ppm or less; such as a resolving power (FWHM) of 25,000 or higher and accuracy of about 3 ppm or less. Three exemplary analyzers capable of exhibiting the requisite level of performance for C peptide ions are orbitrap mass analyzers, certain TOF mass analyzers, and Fourier transform ion cyclotron resonance mass analyzers.

Elements found in biological active molecules, such as carbon, oxygen, and nitrogen, naturally exist in a number of different isotopic forms. For example, most carbon is present as $^{12}C$, but approximately 1% of all naturally occurring carbon is present as $^{13}C$. Thus, some fraction of naturally occurring molecules containing at least one carbon atom will contain at least one $^{13}C$ atom. Inclusion of naturally occurring elemental isotopes in molecules gives rise to multiple molecular isotopic forms. The difference in masses of molecular isotopic forms is at least 1 atomic mass unit (amu). This is because elemental isotopes differ by at least one neutron (mass of one neutron≈1 amu). When molecular isotopic forms are ionized to multiply charged states, the mass distinction between the isotopic forms can become difficult to discern because mass spectrometric detection is based on the mass to charge ratio (m/z). For example, two isotopic forms differing in mass by 1 amu that are both ionized to a 5+ state will exhibit differences in their m/z of only 0.2. High resolution/high accuracy mass spectrometers are capable of discerning between isotopic forms of highly multiply charged ions (such as ions with charges of ±2, ±3, ±4, ±5, or higher).

Figure 6:
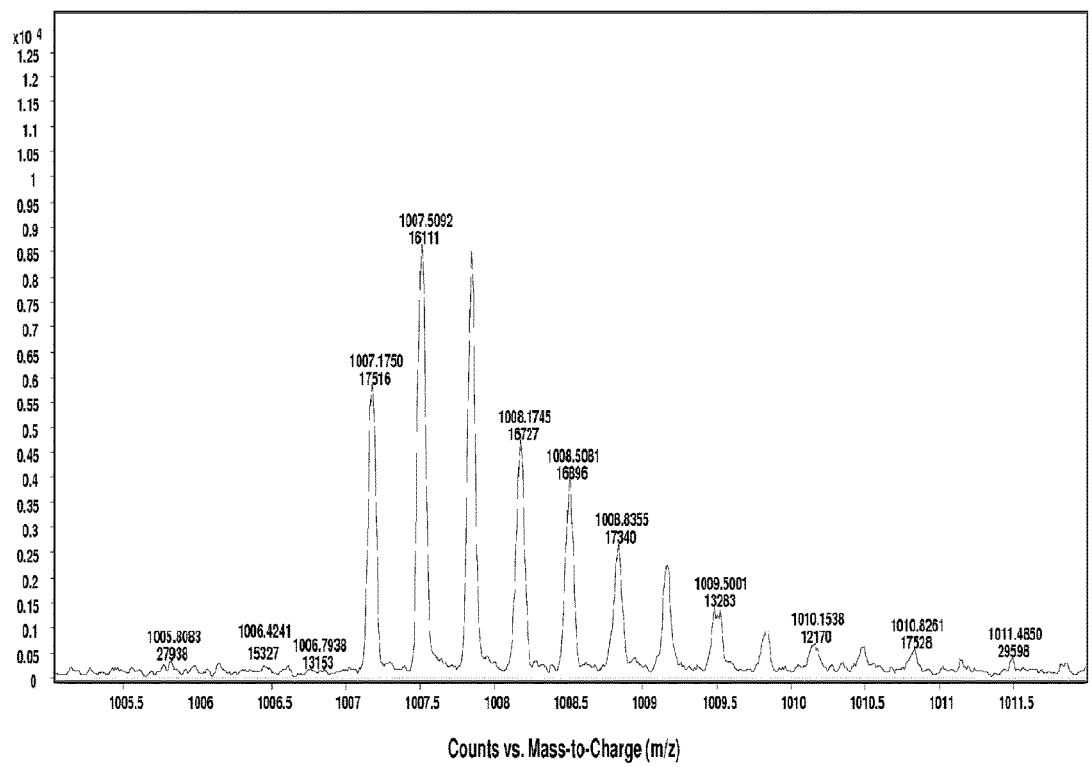
FIG. 6 shows a mass spectra for the C peptide ion with a m/z of about 1007.5±0.50 collected by scanning a high resolution/high accuracy mass spectrometer across the m/z range of about 1005 to 1012. Details are discussed in Example 5.

Due to naturally occurring elemental isotopes, multiple isotopic forms typically exist for every molecular ion (each of which may give rise to a separately detectable spectrometric peak if analyzed with a sensitive enough mass spectrometric instrument). The m/z ratios and relative abundances of multiple isotopic forms collectively comprise an isotopic signature for a molecular ion. In some embodiments, the m/z ratios and relative abundances for two or more molecular isotopic forms may be utilized to confirm the identity of a molecular ion under investigation. In some embodiments, the mass spectrometric peak from one or more isotopic forms is used to quantitate a molecular ion. In some related embodiments, a single mass spectrometric peak from one isotopic form is used to quantitate a molecular ion. In other related embodiments, a plurality of isotopic peaks are used to quantitate a molecular ion. In these later embodiments, the plurality of isotopic peaks may be subject to any appropriate mathematical treatment. Several mathematical treatments are known in the art and include, but are not limited to summing the area under multiple peaks, or averaging the response from multiple peaks. An exemplary spectra demonstrating such a multiple isotopic forms of C peptide ions within a m/z range of about 1007.5 is seen in FIG. 6. As seen in the exemplary spectra, peaks from various isotopic forms are seen at 1007.1750, 1007.5092, 1007.8362, 1008.1745, 1008.5081, 1008.8355. Note, however, that the precise masses observed for isotopic variants of any ion may vary slightly because of instrumental variance.

In some embodiments, the relative abundance of one or more ion is measured with a high resolution/high accuracy mass spectrometer in order to qualitatively assess the amount of C-peptide in the sample. In some embodiments, the one or more ions measured by high resolution/high accuracy mass spectrometry are multiply charged C peptide ions. These multiply charged ions may include one or more of ions with a m/z of about 1510.3 (2+ ion) and about 1007.3 (3+ ion).

Use of high resolution orbitrap analyzers has been reported for qualitative and quantitative analyses of various analytes. See, e.g., U.S. Patent Application Pub. No. 2008/0118932 (filed Nov. 9, 2007); Bredehöft, et al., Rapid Commun. Mass Spectrom., 2008, 22:477-485; Le Breton, et al., Rapid Commun. Mass Spectrom., 2008, 22:3130-36; Thevis, et al., Mass Spectrom. Reviews, 2008, 27:35-50; Thomas, et al., J. Mass Spectrom., 2008, 43:908-15; Schenk, et al., BMC Medical Genomics, 2008, 1:41; and Olsen, et al., Nature Methods, 2007, 4:709-12.

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of C peptide. Methods of generating and using such standard curves are well known in the art and one of ordinary skill is capable of selecting an appropriate internal standard. For example, in preferred embodiments one or more forms of isotopically labeled C peptide may be used as internal standards. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques. Examples of suitable labels include deuterium ($^{2}H$), $^{13}C$, and $^{15}N$. One or more isotopic labels can be incorporated at one or more positions in the molecule and one or more kinds of isotopic labels can be used on the same isotopically labeled molecule.

One or more steps of the methods may be performed using automated machines. In certain embodiments, one or more purification steps are performed on-line, and more preferably all of the purification and mass spectrometry steps may be performed in an on-line fashion.

The following Examples serve to illustrate the invention. These Examples are in no way intended to limit the scope of the methods.

EXAMPLES

Example 1: Sample Preparation

Mock serum samples containing various amounts of human C peptide were prepared by spiking human C peptide in mock serum (40 mg/mL Bovine Serum Albumin (BSA) in Phosphate Buffered Saline (PBS) buffer with 0.002% protease inhibitor AEBSF) at various concentrations for assessment of linear response (discussed below in Example 4).

Human C peptide was also spiked in double charcoal stripped serum obtained from Golden West Biologicals, Inc. at various concentrations to assess linearity of response (discussed below in Example 4).

Example 2: Enrichment of C Peptide Prior to Mass Spectrometry

Sample injection of the above prepared human C peptide-spiked mock and stripped sera was performed with a Cohesive Technologies Aria TX-420 system using Aria OS V 1.6 or newer software.

50 µL samples were introduced into a Strata C-8 on-line SPE column (20 mm×2.0 mm) from Phenomenex, Inc. or equivalent) on-line solid phase extraction column. The solid phase extraction column retained C peptide while letting other serum proteins and large molecules flow through.

C peptide was eluted off the extraction column with 0.1% formic acid in 40% acetonitrile and onto the analytical column (Onyx monolithic C18 analytical column from Phenomenex Inc. (50×2.0 mm). An HPLC gradient was applied to the analytical column, to separate C peptide from other analytes contained in the sample. Mobile phase A was 0.1% formic acid in water and mobile phase B was 0.1% formic acid in acetonitrile. The HPLC gradient started with a 24.0% organic gradient which was ramped to 35.5% in approximately 90 seconds.

The C peptide enriched samples were then subjected to MS/MS or high resolution/high accuracy MS or MS/MS for quantitation of C peptide.

Example 3: Detection and Quantitation of C Peptide by Tandem MS

MS/MS was performed using a Thermo TSQ Vantage MS/MS system (Thermo Electron Corporation). The following software programs, all from Thermo Electron, were used in the Examples described herein: TSQ Ultra Quantum V 1.4.1 or newer, Xcalibur V 2.0 or newer, and LCQuan V 2.5 or newer. Liquid solvent/analyte exiting the analytical column flowed to the heated nebulizer interface of the MS/MS analyzer. The solvent/analyte mixture was converted to vapor in the heated tubing of the interface. Analytes were ionized by ESI.

Figure 2:
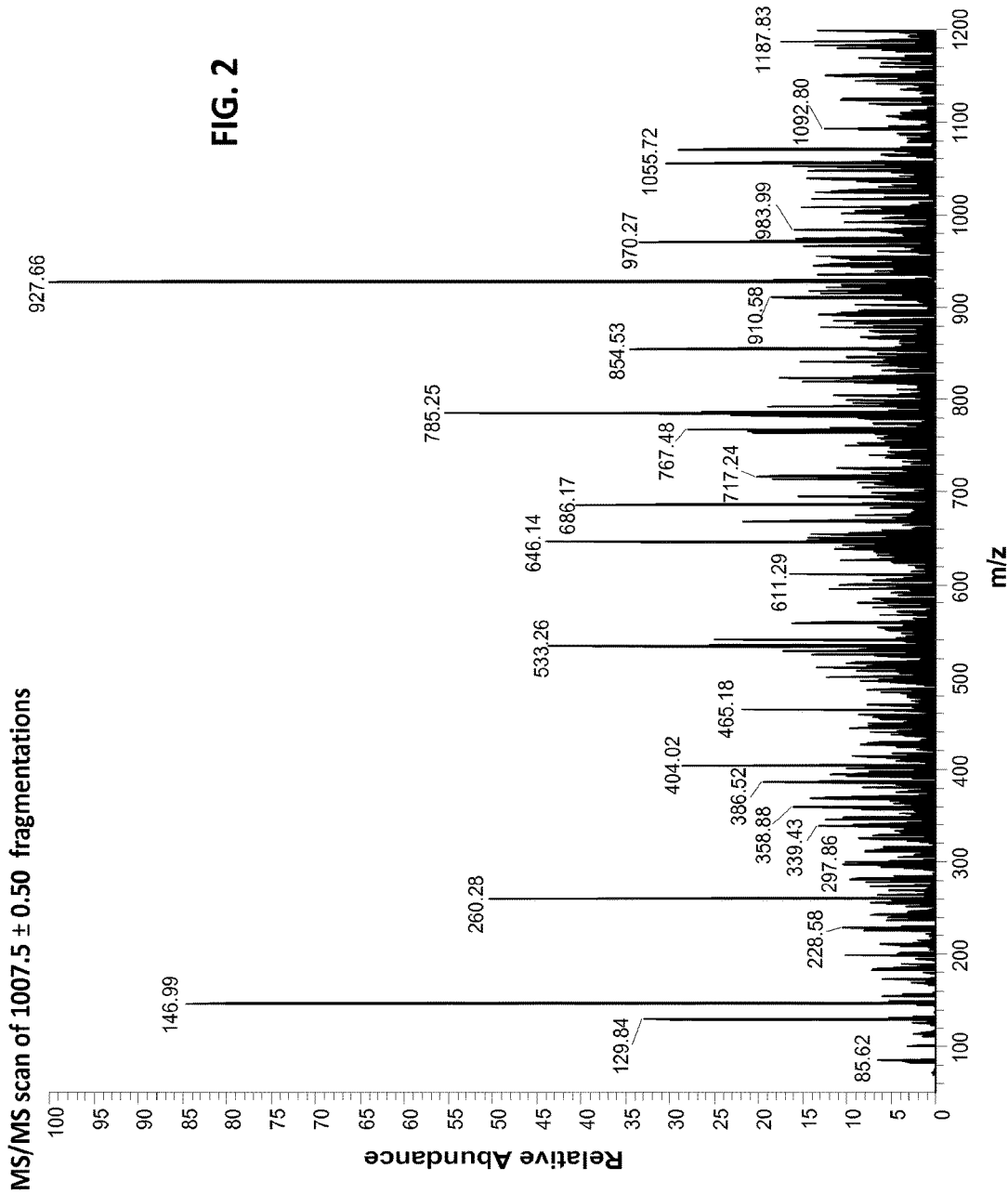
FIG. 2 shows an exemplary fragmentation spectra (product ion scan) for fragmentation of a C peptide precursor ion with a m/z of about 1007.5±0.50 across the m/z range of about 50 to 1200. Details are discussed in Example 3.

Ions passed to the first quadrupole (Q1). Several possible C peptide precursor ions were observed at Q1 as peaks of 1007.5, 1510.38. An exemplary Q1 spectra is seen in FIG. 1. A triply charged C peptide precursor ion with a m/z of 1007.5±0.50 was selected for fragmentation. Ions entering quadrupole 2 (Q2) collided with argon gas (at a collision cell energy of 20 V) to generate ion fragments, which were passed to quadrupole 3 (Q3) for further selection. An exemplary fragmentation spectra collected from a Q3 scan (product ion scan) is shown in FIG. 2. The following mass transitions were observed for fragmentation of the 1007.5±0.50 precursor ion.

TABLE 1

| Mass Transitions Observed for C Peptide (Positive Polarity) | | |
|---|---|---|
| Analyte | Precursor Ion (m/z) | Product Ions (m/z) |
| C peptide | 1007.5 ± 0.50 | 927.6 ± 0.50, 785.4 ± 0.50, 646.1 ± 0.50 |

Of the observed transitions, three were monitored in MRM mode and summed for quantitative analysis: the precursor ion of 1007.5±0.50 to 927.6±0.50, 785.4±0.50, and 646.1±0.50. Although quantitation was accomplished by monitoring three mass transitions, quantitation may be accomplished by monitoring as few as a single mass transition. Conversely, additional mass transitions may be selected to replace or augment, in any combination, any of the above monitored transitions.

Example 4: Tandem MS Data Analysis for Quantitation of C Peptide

C peptide quantitation via monitoring the indicated transitions with a triple quadrupole tandem mass spectrometer was conducted on C peptide spiked mock serum samples and spiked stripped serum samples.

Figure 3:
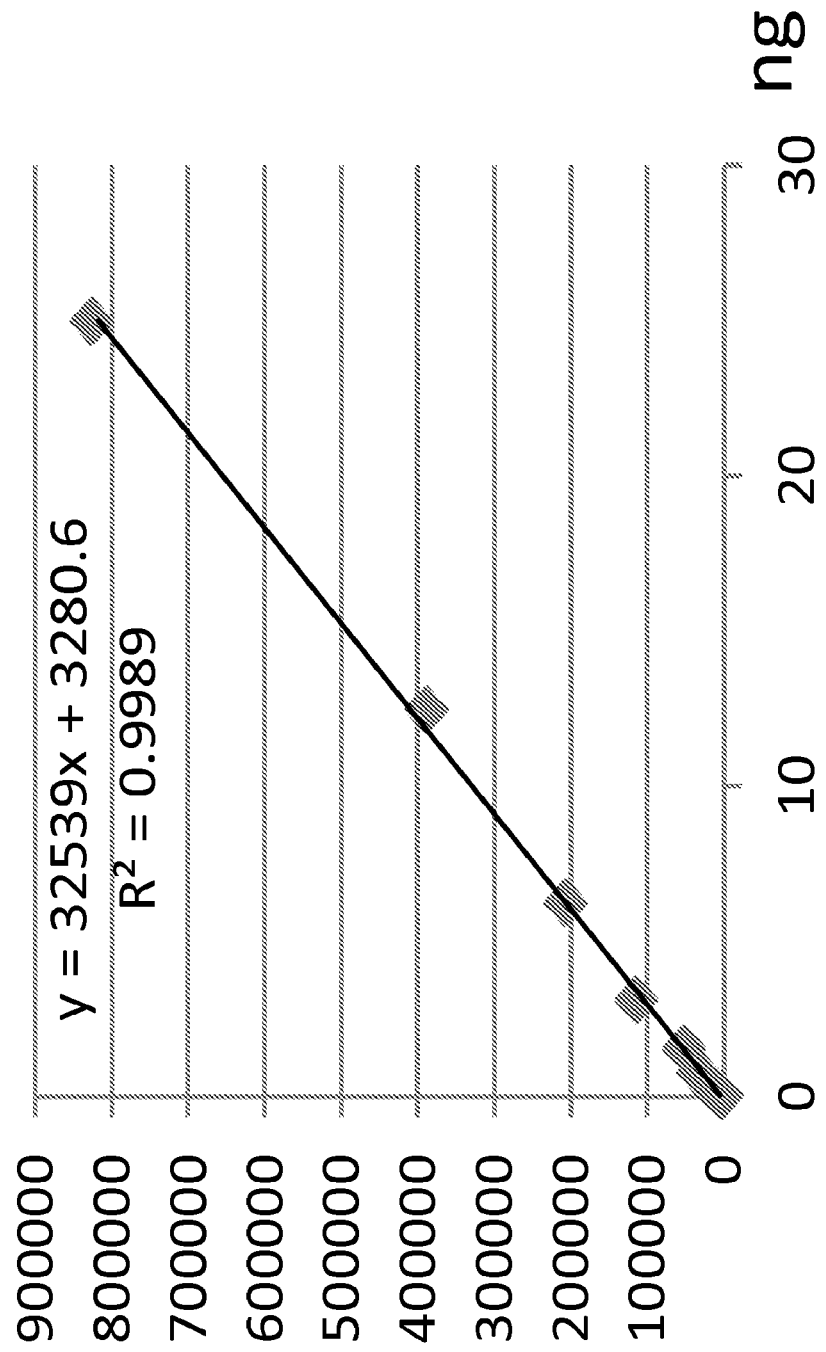
FIG. 3 shows a plot of the linearity of quantitation of C peptide in spiked mock serum standards measured with MS/MS. Details are described in Example 4.
Figure 4:
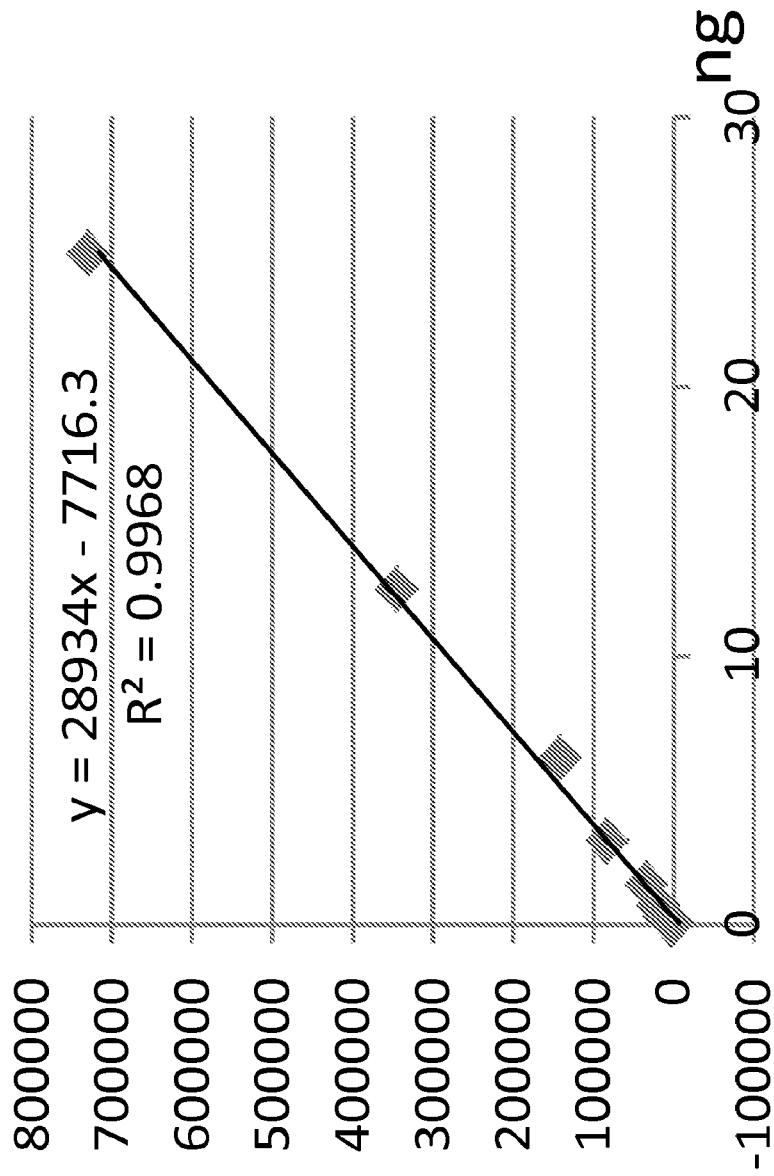
FIG. 4 shows a plot of the linearity of quantitation of C peptide in spiked stripped serum samples measured with MS/MS. Details are described in Example 4.

To establish the linearity of C peptide detection in the assay, several spiked mock serum standards and spiked stripped serum samples were analyzed across a concentration range of about 1 ng/mL to about 500 ng/mL. Graphs showing the linearity of the data for C peptide detection in spiked mock serum standards and spiked stripped serum samples are shown in FIGS. 3 and 4, respectively. The goodness of fit ($R^2$) for C peptide was determined to be 0.998 in mock serum, and 0.996 in stripped serum.

Example 5: Detection of C Peptide by High Resolution/High Accuracy MS

High resolution/high accuracy MS was performed using an Agilent TOF MS system (Agilent Technologies, Inc.). This system employs an QTOF MS analyzer capable of high resolution/high accuracy MS. The instrument exhibits resolution of approximately 10,000 FWHM, and mass accuracy of approximately 50 ppm while measuring C peptide.

Figure 5A:
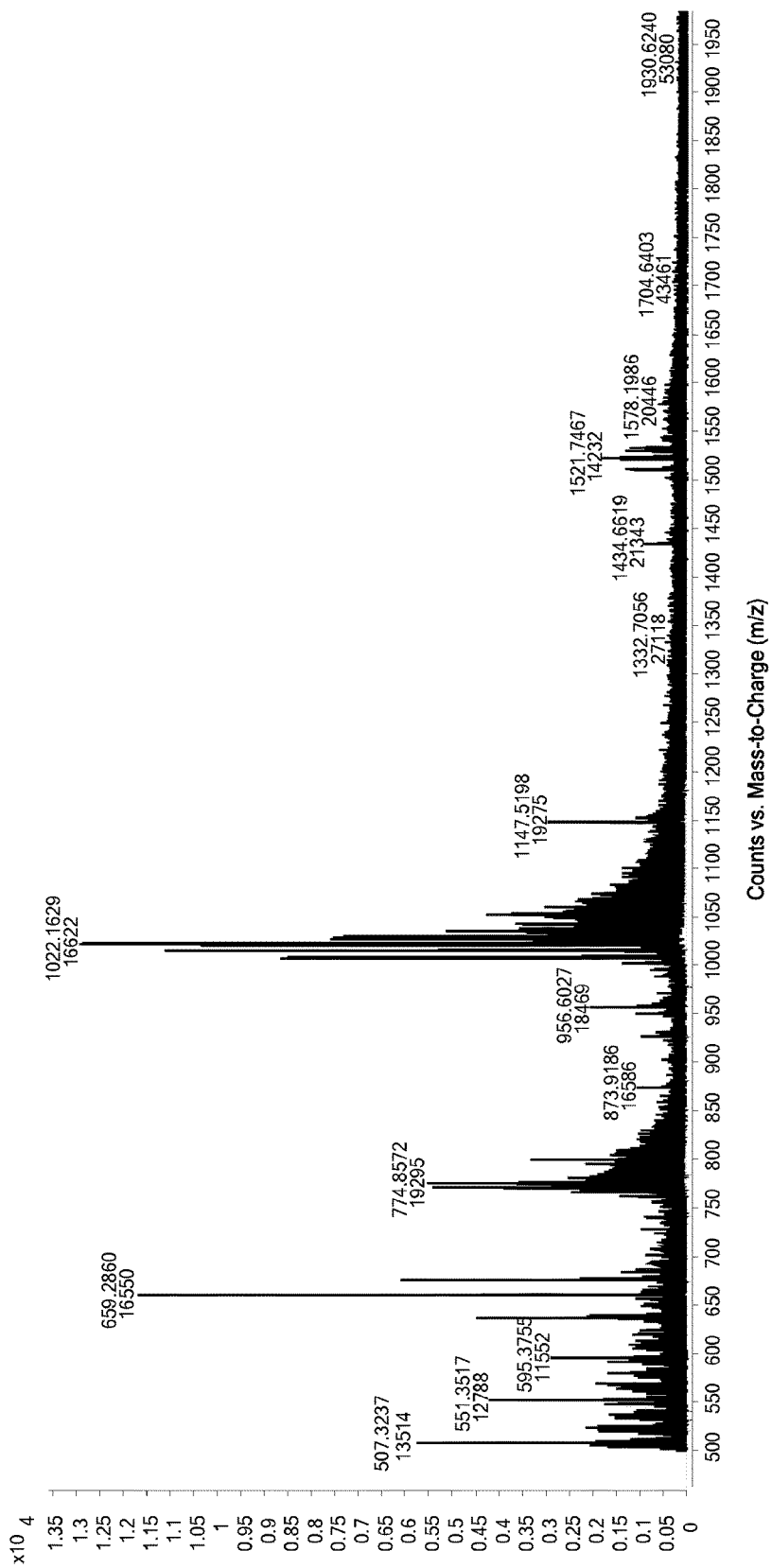
FIGS. 5 A-C show mass spectra for the ionization of C peptide and its sodium adducts collected by scanning a high resolution/high accuracy mass spectrometer across the m/z range of about 500 to 2000, 1005-1040, and 1519-1526, respectively. Details are discussed in Example 5.
Figure 5B:
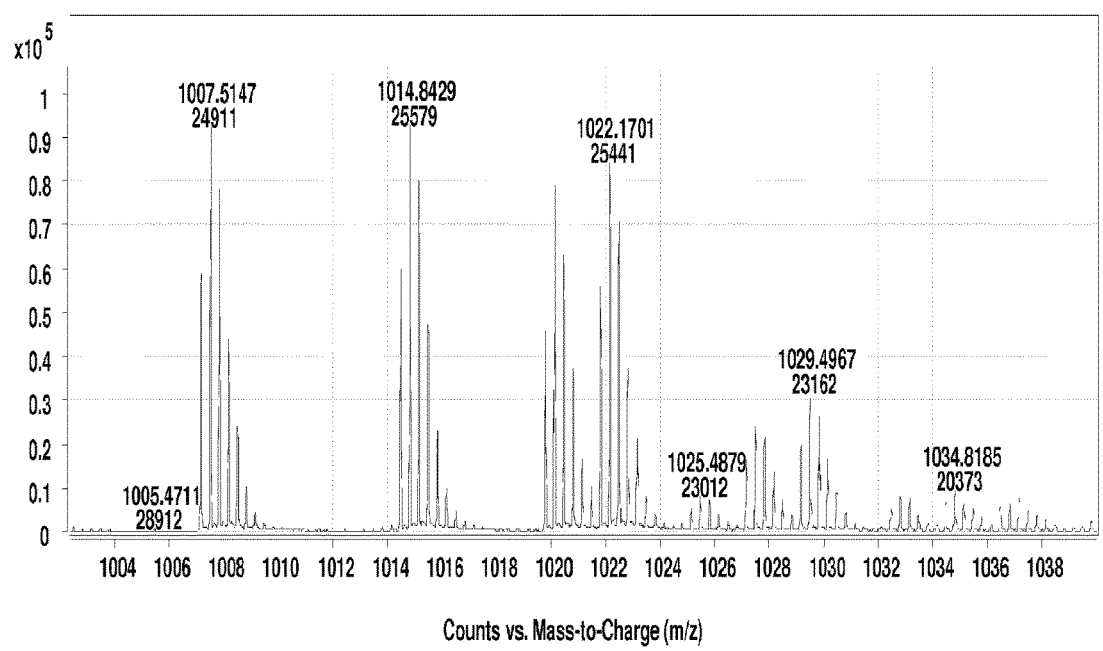
Figure 5C:
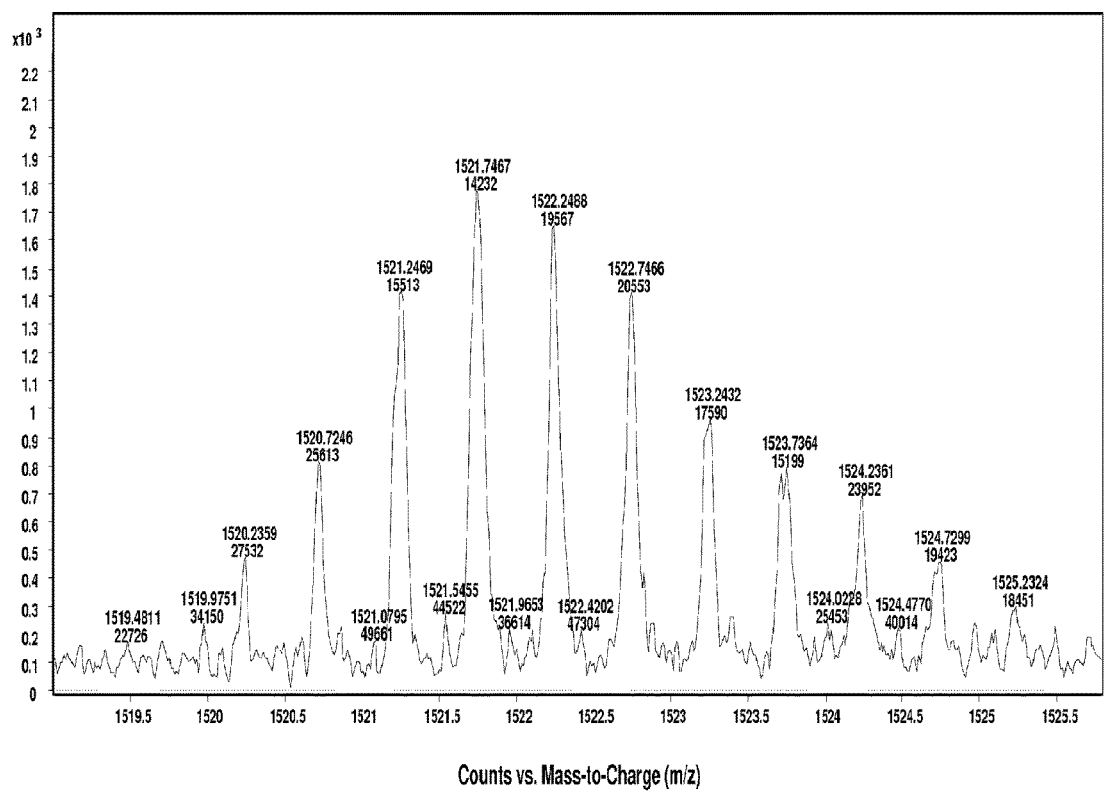

Ionization is conducted with an ESI source in positive ion mode. Multiply charged C peptide ions were observed with m/z of 1510.3±0.50 (for the 2+ ion) and 1007.5±0.50 (for the 3+ ion). An exemplary high resolution/high accuracy spectra across the range of about 500 to 2000, 1005-1040, and 1519-1526, m/z showing C peptide ions is seen in FIGS. 5A-5C respectively.

Data was collected for the ion with m/z of 1007.5±0.50 for quantitation of C peptide. A high resolution scan of this ion was collected and used to confirm the relative abundances of the predicted natural isotopic distribution. An exemplary high resolution/high accuracy spectra across the range of about 1005 to 1012 is shown in FIG. 6.

Example 6: High Resolution/High Accuracy MS Data Analysis for Quantitation of C Peptide C peptide quantitation via monitoring the indicated transitions with a high resolution/high accuracy mass spectrometer was conducted on C peptide spiked mock serum samples and spiked stripped serum samples.

Figure 7:
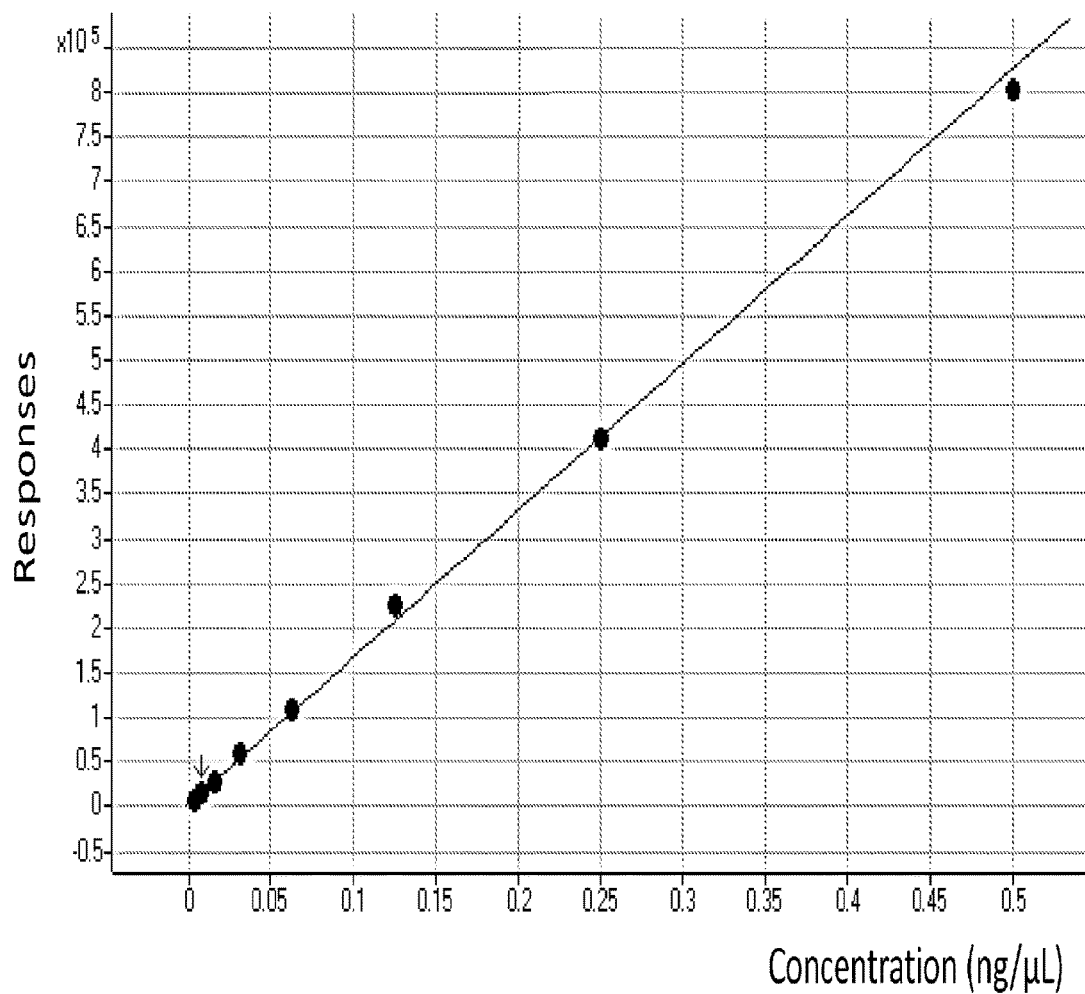
FIG. 7 shows a plot of the linearity of quantitation of C peptide in spiked mock serum standards measured with high resolution/high accuracy MS. Details are described in Example 6.
Figure 8:
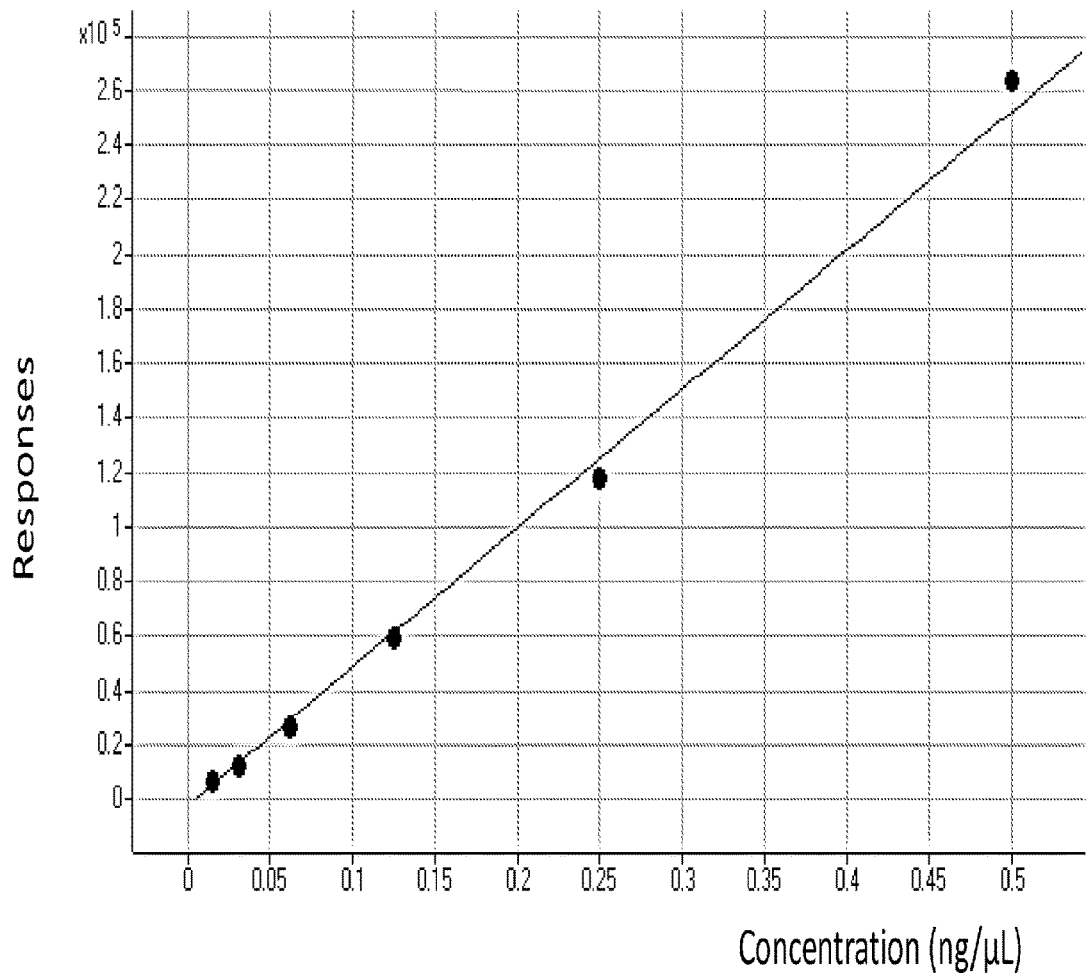
FIG. 8 shows a plot of the linearity of quantitation of C peptide in spiked stripped serum samples measured with high resolution/high accuracy MS. Details are described in Example 6.

To establish the linearity of C peptide detection in the assay, several spiked mock serum standards and spiked stripped serum samples were analyzed across concentration ranges of about 3.9 ng/mL to about 500 ng/mL (spiked mock serum) and about 31.25 ng/mL to about 500 ng/mL (spiked stripped serum). Graphs showing the linearity of the data for C peptide detection in spiked mock serum standards and spiked stripped serum samples are shown in FIGS. 7 and 8, respectively. The goodness of fit ($R^2$) for C peptide was determined to be 0.998 in spiked mock serum, and 0.996 in spiked stripped serum.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of C peptide in a sample by tandem mass spectrometry, the method comprising:
    (a) subjecting a sample suspected of containing C peptide to solid phase extraction (SPE) to obtain a fraction enriched in C peptide;
    (b) subjecting the enriched C peptide to an ionization source under conditions suitable to generate one or more C peptide ions detectable by mass spectrometry;
    (c) determining the amount of one or more C peptide ions by tandem mass spectrometry;
    wherein the amount of ions determined in step (c) is related to the amount of a C peptide in said sample.

2. The method of claim 1, wherein the sample is subjected to high performance liquid chromatography (HPLC) prior to ionization.

3. The method of claim 2, wherein said SPE and HPLC are conducted with on-line processing.

4. The method of claim 1, wherein said ionization source is an electrospray (ESI) ionization source.

5. The method of claim 1, wherein said sample comprises a biological sample.

6. The method of claim 1, wherein said sample is from a human.

7. The method of claim 1, wherein said sample comprises a body fluid sample.

8. The method of claim 1, wherein said sample comprises plasma or serum.

9. The method of claim 1, wherein said one or more ions detected in step (c) comprise a precursor ion with a mass to charge ratio (m/z) of about 1007.5±0.5.

10. The method of claim 1, wherein said one or more C peptide ions comprise two or more fragment ions selected from the group consisting of 927.6±0.5, 785.4±0.5, and 646.1±0.5.

11. The method of claim 10, wherein relating said ions determined in step (c) to the amount of C peptide in the sample comprises summing the amount of said two or more fragment ions.

\* \* \* \* \*